(12) United States Patent
Barth et al.

(10) Patent No.: US 6,506,795 B1
(45) Date of Patent: Jan. 14, 2003

(54) WOOD PRESERVATIVES

(75) Inventors: Volker Barth, Ludwigshafe (DE); Helmut Hartner, Dirmstein (DE); Volker Beez, Bürstadt (DE)

(73) Assignee: WEYL GmbH (DE)

( * ) Notice: Subject to any disclaimer, the term of this patent is extended or adjusted under 35 U.S.C. 154(b) by 1127 days.

(21) Appl. No.: 08/622,085

(22) Filed: Mar. 26, 1996

(30) Foreign Application Priority Data

Apr. 28, 1995 (DE) .......................... 195 15 211

(51) Int. Cl.$^7$ .................. A01N 37/02; A01N 55/02; A01N 33/04; A01N 59/14
(52) U.S. Cl. .................. 514/494; 514/64; 514/499; 514/500; 514/557; 514/558; 514/560; 424/78.08; 424/630; 424/632; 424/633; 424/634; 424/635; 424/637; 424/638; 424/641; 424/657; 424/658; 424/659; 424/660; 428/540; 428/541
(58) Field of Search ................... 514/494, 499, 514/557, 558, 560, 64, 500; 424/630, 641, 657, 660, 78.08, 632–635, 637, 638, 658, 659; 428/540, 541

(56) References Cited

U.S. PATENT DOCUMENTS 5,246,716 A * 9/1993 Sedun et al. ................. 424/713
5,304,237 A * 4/1994 Barth et al. ................. 106/18.3

* cited by examiner

*Primary Examiner*—John Pak
(74) *Attorney, Agent, or Firm*—Bierman, Muserlian and Lucas

(57) ABSTRACT

A chromium-free wood preservative consisting essentially of 1 to 35% by weight of a mixture of 25 to 75 parts by weight of a fatty amine ethoxylate and 75 to 25 parts by weight of at least one member of the group consisting of an unsaturated fatty acid of 3 to 25 carbon atoms and their copper and zinc salts and water.

14 Claims, No Drawings

WOOD PRESERVATIVES

DE-C 34 47 027 describes wood preservatives which are comprised of copper and boron compounds and contain for each gram-atom of copper, 0.5 to 2.5 gram atoms of boron and 2 to 10 moles of an alkanol amine. According to DE-A 35 20 394, a copper salt solution is adjusted with an alkanol amine and potentially an alkali metal base to a pH-value of at least 8. Such agents can additionally contain a boron salt and another water-soluble fungicide, particularly up to 25 percent by weight of the finished agent, of quaternary ammonium salts. The copper salts are fixed through neutralization with wood constituents or $CO_2$ from the atmosphere. In spite of the additional use of the quaternary ammonium salts, the effect of these agents, particularly the long-term effect, is not sufficient to achieve the protective effect desired by the consumer.

The addition, obvious per se, of further fungicidal agents also does not yield significant improvement, particularly the problem with the ubiquitous copper-resistant fungus of the genus porea is unsolved. In wood impregnated with the copper-alkanol amine system, these fungi convert the copper into a water soluble form which is subsequently washed out.

Only the agent known from DE-A 42 28 352 comprising copper salts, alkanol amines and polymer quaternary ammonium borates solves this problem, but this agent also has disadvantages. On the one hand, this disadvantage is one common to all wood preservatives based on copper and boron, namely that boron salts are washed out in time and thus their effect is lost. For another, the disadvantage involves the particularity of the polymer quaternary ammonium borate that in an impregnation installation, it causes the resins to be leached out of the wood whereby the wood protection effect due to the resins is lost and the leached out resins contaminate the installations and impair their ability to function.

OBJECTS OF THE INVENTION

It is an object of the invention to provide a chromium-free wood preservative without the prior art defects.

It is another object of the invention to provide an improved method of impregnating wood and the wood products produced thereby.

These and other objects and advantages of the invention will become obvious from the following detailed description.

THE INVENTION

The novel chromium-free wood preservatives of the invention consist essentially of 1 to 35% by weight of a mixture of 25 to 75 parts by weight of a fatty amine ethoxylate and 75 to 25 parts by weight of at least one member of the group consisting of an unsaturated fatty acid of 3 to 25 carbon atoms and their copper and zinc salts and water.

The wood preservatives of the invention have the advantage that the copper salts do not have their long-term effect diminished by the action of copper resistant-fungi. If the wood preservative contains both copper and boron salts, the problem of washing out of the boron salts is significantly reduced. Moreover, the agents of DE-A 42 28 352 are improved so that the resins are not leached out.

It was found that the effect of wood preservatives based on copper salts is no longer reduced through copper-resistant fungi if these wood preservatives comprise 2–35 per by weight of a product comprising 25–75 parts by weight of fatty amine ethoxylate and 75–25 parts by weight of unsaturated fatty acid with 3–25, preferably with 9–15 C atoms. Due to this addition, copper salts penetrate deeply into the wood and experience a type of fixing in the wood whereby they are not decomposed or metabolized by the fungi. The degree to which boron salts are washed out is significantly reduced so that long-term protection of the wood is given.

It was found, in addition, that products comprising 25–75 parts by weight of fatty amine ethoxylate parts and 75–25 parts by weight of unsaturated fatty acids with 3–25, preferably with 9–15 C atoms are suitable as wood preservatives with fixing, fungicidal and insecticidal effects. The fungicidal effect of some unsaturated carboxylic acids, such as acrylic acid or undecylenic acid is known, but it is surprising that the addition products of these acids with fatty amine ethoxylate have fungicidal as well as also insecticidal effects and that they are fixed in wood. It was furthermore found that the products of fatty amine ethoxylate and unsaturated fatty acids show improved fungicidal action not only with copper salts but also with zinc salts.

In the simplest case, the wood preservatives of the invention comprise a 1 to 35% by weight of an aqueous solution of a mixture of 25–75 parts by weight of fatty amine ethoxylate and 75–25 parts by weight of unsaturated fatty acids of 3–25, preferably with 9–15 carbon atoms. In an improved form, the wood preservatives of the invention comprise a 1 to 35% by weight of an aqueous solution of a water soluble copper and/or zinc salt and 2 to 35% by weight of the product of fatty amine ethoxylate and unsaturated fatty acid. The same effect profile is attained if, instead of the unsaturated fatty acids, their copper and/or zinc salts are used.

The penetration by the copper and by the zinc is improved if they are complexed with ammonia, amines, or alkanol amines. This effect is especially strong if the wood preservatives also contain boron salts as additional fungicidal substances. For the complexing, monoethanol amine is preferably used in these agents.

In general, the wood preservatives of the invention can also contain additional fungicidal and/or insecticidal agents known per se. An undesirable interaction between such agents and the employed products of fatty amine ethoxylate and unsaturated fatty acids has not been observed so far, either with inorganic or organic fungicidal or bactericidal agents.

For environmental reasons, boron compounds, particularly boron salts, are preferred as fungicidally acting components. Thus, the preferred wood preservatives comprise at least one copper and/or zinc salt, at least one boron compound, optionally additional insecticidal and/or fungicidal agents, monoethanol amine, all compounds in quantities known per se, as well as 2 to 35 percent by weight of a mixture of fatty amine ethoxylate and unsaturated fatty acid as defined above.

The preferred boron compound is a polymer quaternary ammonium borate, such as is known from EP-A 0 355 316 and DE-A 42 28 352. The especially preferred wood preservatives are accordingly stable aqueous emulsions with the following composition:

| | |
|---|---|
| Copper salt | 10–25 percent by weight |
| Ethanol amine | 30–40 percent by weight |
| Boric acid, Na borate | 0–8 percent by weight |

-continued

| | |
|---|---|
| Polymer quaternary ammonium borate | 5–40 percent by weight |
| Product of fatty amine ethoxylate and unsaturated fatty acid | 2–35 percent by weight |
| Water | 10–50 percent by weight |

These agents are available in the form of concentrates which before use are diluted with water to a concentration of 1 to 20 percent of the aqueous concentrate, preferably 1 to 4 percent, when used in vacuum pressure processes and of 3 to 15 percent when used in processes at ambient pressure.

These agents have further unexpected properties since in machine impregnation processes, no resins are extracted from the wood or the extracted resins detached from the surface are so well emulsified that they are again transported into the wood with the penetrating wood preservative. The impregnation installations are thereby kept free of any loading by resins.

The addition of the products of fatty amine ethoxylate and unsaturated fatty acids surprisingly improves the ability of the wood preservative to be stained. In particular, agents with quaternary ammonium salts could previously only be poorly stained and staining them brown was previously virtually impossible since such mixtures separate into several phases. By adding approximately 2 to 35 percent of the listed products, stable homogeneously stained emulsions result which also yield uniform staining of the impregnated wood when applied.

The fatty amine ethoxylate/fatty acid products used in the wood preservatives of the invention are produced by mixing fatty amine ethoxylates with ethylenic unsaturated fatty acids in a weight ratio of 75:25 to 25:75, preferably at a ratio of 50:50, i.e. the carboxyl groups and the amino groups should be present approximately in stoichiometric ratios. Deviations of up to 20% are acceptable.

Fatty amine ethoxylates are conversion products of fatty amines, particularly stearyl amine, coconut oil amine or tallow amine with ethylene oxide and ethoxylates with an ethylene oxide (EO) content of 5 to 35 units per molecule are formed. The ethoxylates conventionally used are mixtures of differently ethoxylated fatty amines or fatty amine mixtures.

Ethylenic unsaturated fatty acids which can be used are fatty acids with 3 to 30, preferably 9 to 15, carbon atoms which are simply or multiply unsaturated. Examples of such acids are acrylic acid, methacrylic acid, butenoic, acid, citronellic acid, sorbic acid, linoleic acid, linolenic acid or particularly undecylenic acid.

In the following examples, these are described several preferred embodiments to illustrate the invention. However, it is to be understood that the invention is not intended to be limited to the specific embodiments.

Example 1

Coconut oil amine ethoxylates, ⅓ each, with an ethylene oxide (EO) content of 10, 15 and 20 ethylene oxide units per molecule and undecylenic acid were mixed in equal parts by weight while stirring. The product obtained was a highly fluid, water-soluble liquid having a pH-value of 7.

Example 2

Using the procedure of Example 1, stearyl amine ethoxylate, ¼ each, having an EO content of 10, 15, 20 and 25 ethylene oxide units and undecylenic acid were mixed in equal parts by weight. The product was a highly fluid, water-soluble liquid having a pH-value of 7.

Example 3

Using the procedure of Example 1, coconut amine ethoxylate, ⅓ each, with an EO content of 10, 15 and 20 ethylene oxide units and oleic acid were mixed in equal parts by weight. The product obtained was a highly fluid, water-soluble liquid with a pH-value of 7.

Example 4

Using the procedure of Example 1, coconut fatty amine ethoxylate, ⅓ each with an EO content of 10, 15 and 20 ethylene oxide units and stearic acid were mixed in equal parts by weight. The product obtained was poorly soluble in water and formed sediments.

Example 5

The product of Example 1 was introduced as an aqueous solution at different concentrations into test blocks of pine wood and tested analogously to EN 113 for wood-destroying fungi. The limits of the effectiveness (mass loss 0%) were determined before and after subjecting the samples to washing-out tests according to EN 84.

Test fungus: *Coniophora puteana* (mass loss of the non-treated comparison samples: 20.5%).

Results:

| | Preservative absorption [kg/m³] |
|---|---|
| Limits of effectiveness before being subjected to washing-out Concentration of impregnating solution [%] | |
| 1.0–1.25 | 6.9–8.8 |
| Limits of effectiveness after being subjected to washing-out Concentration of impregnating solution [%] | |
| 0.63–1.0 | 4.5–7.1 |

Various modifications of the compositions and method of the invention may be made without departing from the spirit or scope thereof and it should be understood that the invention is to be limited only as defined in the appended claims.

What we claim is:

1. A chromium-free wood preservative consisting essentially of 1 to 35% by weight of a mixture of 25 to 75 parts by weight of a fatty amine ethoxylate and 75 to 25 parts by weight of at least one member of the group consisting of an unsaturated fatty acid of 3 to 25 carbon atoms and their copper and zinc salts and water.

2. A wood preservative of claim 1 additionally containing 1 to 35% by weight of a water-soluble salt of a member selected from the group of copper, zinc and boron.

3. A wood preservative of claim 2 wherein the copper or zinc is complexed with a member selected from the group consisting of ammonia, amines and alkanol amines.

4. A wood preservative of claim 1 further containing at least one member of the group consisting of a fungicide and insecticide.

5. A wood preservative of claim 1 further containing at least one water soluble boron compound.

6. A wood preservative of claim 5 wherein the boron compound is a polymer quaternary ammonium borate.

7. A wood preservative of claim 1 wherein the fatty acid amine ethoxylate is selected from the group consisting of stearyl amine ethoxylate of 10 to 30 ethylene oxide units and coconut oil amine ethoxylate of 10 to 30 ethylene oxide units.

8. A wood preservative of claim 1 wherein the unsaturated fatty acid is undecylenic acid.

9. A wood preservative of claim 7 wherein the unsaturated fatty acid is undecylenic acid.

10. A method of preserving wood comprising impregnating the wood with a wood preservative of claim 1.

11. The method of claim 10 wherein the fatty acid amine ethoxylate is selected from the group consisting of stearyl amine ethoxylate of 10 to 30 ethylene oxide units and coconut oil amine ethoxylate of 10 to 30 ethylene oxide units.

12. The method of claim 11 wherein the unsaturated fatty acid is undecylenic acid.

13. A wood product impregnated with a wood preservative of claim 1.

14. A wood product impregnated with a wood preservative of claim 9.

* * * * *